US006921633B2

(12) United States Patent
Baust et al.

(10) Patent No.: US 6,921,633 B2
(45) Date of Patent: Jul. 26, 2005

(54) METHODS AND COMPOSITIONS FOR THE PRESERVATION OF CELLS, TISSUES OR ORGANS IN THE VITREOUS STATE

(75) Inventors: John M. Baust, Candor, NY (US); John G. Baust, Candor, NY (US); Robert VanBuskirk, Apalachian, NY (US); Aby J. Mathew, Binghamton, NY (US)

(73) Assignee: Biolife Solutions Incorporated, Binghamton, NY (US)

( * ) Notice: Subject to any disclaimer, the term of this patent is extended or adjusted under 35 U.S.C. 154(b) by 0 days.

(21) Appl. No.: 10/298,497

(22) Filed: Nov. 18, 2002

(65) Prior Publication Data

US 2004/0096813 A1 May 20, 2004

(51) Int. Cl.⁷ .............................. A01N 1/00; A01N 1/02
(52) U.S. Cl. ............................................. 435/1.3; 435/2
(58) Field of Search .......................... 435/1.1, 1.2, 1.3, 435/2

(56) References Cited

U.S. PATENT DOCUMENTS

| | | | |
|---|---|---|---|
| 4,559,298 A | 12/1985 | Fahy .............................. | 435/1 |
| 5,217,860 A | 6/1993 | Fahy et al. ..................... | 435/1 |
| 5,723,282 A | 3/1998 | Fahy et al. ................... | 435/1.3 |
| 5,821,045 A | 10/1998 | Fahy et al. ................... | 435/1.2 |
| 5,962,214 A | 10/1999 | Fahy et al. ................... | 435/1.3 |
| 6,045,990 A | 4/2000 | Baust et al. ................... | 435/1.1 |
| 6,187,529 B1 | 2/2001 | Fahy et al. ................... | 435/1.2 |
| 6,303,388 B1 | 10/2001 | Fahy .......................... | 436/518 |
| 6,395,467 B1 | 5/2002 | Fahy et al. ................... | 435/1.3 |

OTHER PUBLICATIONS

Wang et al., "Mechnaisms of Calcium–Induced Disintegrative Globulization of Rat Lens Fiber Cells" Investigative Ophthalmolog & Visual Science 37 (5) : 915–22 (1996).*
Ren et al., "The Crystallization Kinetics and the Critical Cooling Rates for Vitrification of Cryoprotective Solutions", Cryogenics 30 (Sep. Supp.) : 536–40 (1990).*
Rich et al., "Corneal Tolerance of Vitrifiabel Concentration of Glycerol", Cryobiology 29 : 153–64 (1992).*

Evan & Littlewood, "A Matter of Life and Cell Death", Science (1998) V. 281 p. 1317–22.
Kerr, et al., "Apoptosis: Its Significance in Cancer and Cancer Therapy", Cancer (1994) V. 73 p. 2013–26.
Lane et al., "Addition of Ascorbate During Cryopreservation Stimulates Subsequent Embryo Development" Human Reproduction, vol. 17, No. 10, pp. 2686–2693, Oct. 2002.
DeBiasi et al., "Calpain Inhibition Protects Against Virus–Induced Apoptic Mycocardial Injury" 2001, J. Virol. 351–361, 75.
Pahernik et al., "Hypothermic Storage of Pig Hepatocytes: Influence of Different Storage Solutions and Cell Density", 1996, Cryobiology 33: 552–566.
Fisher et al., "Cold–Cryopreservation of Dog Liver and Kidney Slices" 1996, Cryobiology 33: 163–171.
Rodriguez et al, "Protective Effect of Glutathione (GSH) Over Glutathione Monoethyl–Ester (GSH–E) on Cold Preservation of Ioslated Rat Liver Cells" 1995, Cell Transplant. 4: 245–251.
Levi et al., "Cold Storage of Peripheral Nerves: An In Vitro Assay of Cell Viability and Function" 1994, Glia 10:121–131.
Lopukhin et al, "Cold Storage of the Heart with University of Wisconsin Solution and 2, 3–Butanedione Monoxime: Langendorff vs Isolated Working Rabbit Heart Model." 1996, Cryobiology 33: 178–185.
Zhang et al., "The Beneficial Effects of Heat–Shock for Prolonged Hypothermic Storage" 1996, J. Surg. Res. 63: 314–319.
Carbognani et al, "Ultrastructural Damage of the Pulmonery Endothelial Cell after Storage In Lung Preservation Solutions. Comparison Between Belzer and Euro–Collins solutions." 1995, J. Cardiovasc. Surg. 36:93–95.
Katz et al, "Improved Small Intestinal Preservation After Lazaroid U74389G Treatment and Cold Storage In University of Wisconsin Solution" 1995, Transplantation 59: 694–698.

* cited by examiner

Primary Examiner—Sandra E. Saucier
(74) Attorney, Agent, or Firm—Brown & Michaels, PC

(57) ABSTRACT

The invention provides methods for the hypothermic preservation of cells, tissues and organs. In particular, the invention provides methods for the hypothermic preservation or storage of cells, tissues or organs in the vitreous state.

4 Claims, No Drawings

METHODS AND COMPOSITIONS FOR THE PRESERVATION OF CELLS, TISSUES OR ORGANS IN THE VITREOUS STATE

FIELD OF THE INVENTION

The invention relates to the hypothermic preservation of cells, tissues and organs. In particular, the invention relates to the hypothermic preservation or storage of cells, tissues or organs in the vitreous state.

DESCRIPTION OF BACKGROUND INFORMATION

The preservation of eukaryotic cells, tissues or organs is commonly carried out by chilling them sufficiently to slow or halt metabolic processes that require ongoing support by an organism or the environment to maintain viability. The preservation of cells, tissues or organs by such chilling is generally referred to as hypothermic preservation or hypothermic storage.

There are two broad types of hypothermic storage for cells, tissues or organs. The first involves storage at temperatures above the freezing point of the solution or medium in which the sample is suspended, immersed or with which the sample is perfused. For example, such temperatures may be in the range of about 17° C. to 0° C. Such conditions are appropriate only for short term storage, generally on the order of hours to several days to about a week.

The second broad type, cryogenic storage, involves storage at lower temperatures (below 0° C.), for example, as low as −80° C. to −196° C. Storage under these conditions is more appropriate for longer periods of time. In this second broad category, there are two general subclasses of preservation approach. The first sub-class involves the freezing of the samples in a medium or solution that permits the formation of ice crystals. For this approach, cryoprotective agents (e.g., dimethyl sulfoxide (DMSO), glygerol) are added that mitigate the effect of the formation of ice crystals, essentially by causing dehydration of the cells that prevents intracellular water crystal formation. This approach will be referred to herein as "cryopreservation."

The second sub-class involves immersing or suspending cells or tissues in, or perfusing organs with, a solution comprising an agent that prevents ice nucleation within the extracellular and intracellular environment thereby preventing ice formation Reducing the temperature of such a solution below its glass transition temperature (Tg) results in the formation of a glass or vitreous state, which is defined as an amorphous solid without crystalline structure. That is, the second sub-category involves preservation in a solution that forms a glass or vitreous state, instead of freezing in a crystalline state. In this approach, the cell, tissue or organ never comes in contact with or experiences the formation of extra- or intracellular ice crystals. This approach is referred to herein as "vitrification." In such a solution, an amorphous glass forms when the solution is cooled below the glass transition temperature (Tg), and the formation of this amorphous glass or vitreous state precludes the subsequent alignment of the water molecules that is necessary for the formation of crystalline ice, even when temperatures are reduced below the homogeneous nucleation temperature.

The basic challenge of hypothermic storage is to preserve the material in a state that can be reversed without causing extensive cell damage or cell death. Approaches that minimize the formation of ice crystals in or around cells are well known to aid in the survival and ultimate recovery of material stored at hypothermic temperatures. However, even when ice crystal formation is essentially completely avoided, as in the vitrification approach, there is an associated degree of cell death. Cell death is known to occur by two different mechanisms. The first, necrotic cell death or necrosis, is not mediated by a specific cellular pathway. Necrosis is characterized by the loss of cell membrane integrity resulting in cell swelling, and is caused by a number of pathological agents. DNA in cells that undergo necrosis is cleaved in a random fashion. Thus, the DNA from cells that have undergone necrosis appears as a continuous smear when subjected to gel electrophoresis. The second cell death mechanism, apoptosis or programmed cell death, is the result of the activation of a specific biochemical pathway involving a cascade of biochemical activation steps that ultimately result in the death of the cell. Apoptosis is characterized by cell shrinkage, intact plasma membranes, and non-random cleavage of DNA at an approximately 180 nucleotide interval, evidenced by a ladder of DNA cleavage products upon gel electrophoresis of genomic DNA. Apoptosis is reviewed, for example, by Kerr et al., 1994, Cancer 73: 2013 and Evan & Littlewood, 1998, Science 281: 1317.

It has recently been determined that the cell death accompanying hypothermic and cryogenic storage involves an apoptotic component. U.S. Pat. No. 6,045,990, incorporated herein by reference, demonstrates, in part, that survival and recovery from cryopreservation can be enhanced by the inclusion of anti-apoptotic agents in the preservation medium.

There is a need in the art for improved methods of hypothermic and cryogenic preservation.

SUMMARY OF THE INVENTION

The invention is drawn to methods and compositions for the preservation of cells, tissues or organs in the vitreous state.

The invention encompasses a method of preserving a eukaryotic cell, tissue or organ comprising: a) contacting the cell, tissue or organ with a hypothermic storage solution, wherein the solution comprises: i) a composition that inhibits apoptosis; and ii) a concentration of a vitrification composition that is sufficient for vitrification of the solution; and b) vitrifying the cell, tissue or organ, wherein the vitrification occurs both within the cell, tissue or organ and in the hypothermic storage solution comprising and comprised by the cell, tissue or organ.

The vitrification is accomplished through use of a hypothermic storage solution comprising an agent that prevents ice nucleation within the extracellular and intracellular environment thereby preventing ice formation and that has a glass transition temperature (Tg) lower than the homogeneous nucleation temperature of the solution. Reduction of the temperature of a sample in a hypothermic storage solution to below the glass transition temperature results in vitrification of the solution and the cell, tissue or organ in that solution. Under these circumstances, there is no crystalline ice formation in or around the cells as the sample becomes a solid. The inclusion of one or more anti-apoptotic agents aids in preventing the apoptotic cell death that normally occurs following this type of preservation.

In another embodiment, the vitrification composition comprises one or more of the following agents that lowers the Tg of an aqueous vitrification solution including but not limited to sucrose, trehalose, lactose, glucose, DMSO, propylene glycol, ethylene glycol, dextrans, glycerol, hydroxyethyl starch, polyvinyl pyrrolidone, formamide, 1-2- propanediol, ethanol, methanol, and polyethylene oxide. Concentrations of these agents may vary with the identity of the agent and with the specific application. For example, the carbohydrates, glycols and dextrans will frequently be present at concentrations of 30% to 60% (w/v), while agents such as DMSO will be present at lower concentrations (e.g., approximately 5–15%) but may exceed 50%.

Vitrification as a method of hypothermic preservation, as well as solutions for vitrification are described, for example, in U.S. Pat. Nos. 4,559,298, 5,217,860, 5,723,282, 5,821, 045, 6,187,529, 6,303,388 and 6,395,467, each of which is incorporated herein by reference.

In another embodiment, the composition that inhibits apoptosis can comprise an agent that interacts with a polypeptide that participates in an apoptotic pathway.

In another embodiment, the agent inhibits the activity of the polypeptide.

In another embodiment, the agent maintains or potentiates the activity of the polypeptide.

In another embodiment, the agent is selected from the group consisting of a caspase inhibitor, a calpain inhibitor, and an inhibitor of nitrous oxide synthase. In a more specific embodiment, the agent is a caspase inhibitor and is selected from the group consisting of: a peptide fluoromethyl ketone (FMK) (e.g., YVAD-FMK (benzyloxycarbonyl tyrosylvalylalanyl aspartic acid fluoromethyl ketone), DEVD-FMK (benzyloxyycarbonyl aspartyl glutamylvalylaspartic acid fluoromethyl ketone), VEID-FMK (benzyloxycarbonyl valylglutamyl isoleucylaspartic acid fluoromethyl ketone), LETD-FMK (benzyloxycarbonyl leucylglutamylthreonylaspartic acid fluoromethyl ketone), LEHD-FMK (benzyloxycarbonyl leucylglutamylhistidylaspartic acid fluoromethyl ketone), Z-LEVD-FMK, WEHD-FMK, AEVD-FMK and LEED-FMK); CHO, a peptide chloromethyl ketone (CMK); DCB (2,6-dichlorobenzoyloxmethyl ketone); AOM (2,6-dimethylbenzoyloxmethyl ketone); and FAOM (2,6-bis(trifluoromethyl)benzoyloxmethyl ketone).

In another more specific embodiment, the agent is a calpain inhibitor and is selected from the group consisting of: Leupeptin; Calpain inhibitors I, II, III, IV and V; Calpeptin; Loxastatin; a peptide chloromethyl ketone and/or a peptide fluoromethyl ketone. Additional equivalent calpain inhibitor agents include, for example, a dipeptidyl alphaketoamide, a dipeptidyl phosphorus derivative; a peptide diazomethylketone, a peptide disulfide, a peptide methyl esters, a peptide acycloxymethyl ketone and a Quinoline carboxamide.

In another embodiment, the composition that inhibits apoptosis may comprise an antioxidant. In a more specific embodiment, the antioxidant is selected from the group consisting of glutathione, N-acetyl cysteine, beta carotene, Vitamin E, D, C, A, Nitric Oxide, L-arginine, and super oxide dismutase.

In another embodiment, the composition that inhibits apoptosis comprises an agent selected from the group consisting of a free radical scavenger, a zinc chelator, and a calcium chelator. In a more specific embodiment, the agent is a free radical scavenger. In a further specific embodiment, the free radical scavenger is selected from the group consisting of Vitamin E, D, C, A, Nitric oxide, L-arginine, super oxide dismutase. Additional free-radical scavengers and similar anti-apoptotic agents are listed in Table II.

The invention further encompasses a hypothermic preservation solution comprising: a) a composition that inhibits apoptosis, and b) a vitrification composition that comprises a concentration of one or more agents that is sufficient for vitrification of the solution when the temperature of the solution is reduced below the Tg of the solution.

In one embodiment, the Tg of the solution is lower than the homogeneous nucleation temperature of the solution.

In another embodiment, the composition that inhibits apoptosis may comprise an agent that interacts with a polypeptide that participates in an apoptotic pathway. In a more specific embodiment, the agent inhibits the activity of the polypeptide. In another specific embodiment, the agent maintains or potentiates the activity of said polypeptide.

In another embodiment, the agent is selected from the group consisting of a caspase inhibitor, a calpain inhibitor, and an inhibitor of nitrous oxide synthase. In a more specific embodiment, the agent is a caspase inhibitor and can be selected, for example, from those listed herein above. In another preferred embodiment, the agent is a calpain inhibitor and can be selected, for example, from those listed herein above.

In another embodiment, the composition that inhibits apoptosis can comprise an antioxidant. In a more specific embodiment, the antioxidant is selected, for example, from glutathione, N-acetyl cysteine, beta carotene, Vitamin E, D, C, A, Nitric oxide, L-arginine, and super oxide dismutase.

In another embodiment, the composition that inhibits apoptosis may comprise an agent selected from the group consisting of a free radical scavenger, a zinc chelator, and a calcium chelator. In a more specific embodiment, the agent is a free radical scavenger. In another specific embodiment, the agent can be selected from Vitamins E, D, C and A, Nitric oxide, L-arginine, super oxide dismutase, and the additional free-radical scavengers and similar anti-apoptotic agents listed in Table II.

As used herein, the term "vitrifying" means establishing a vitreous state in a solution and in cells, tissue or organs suspended in or perfused with that solution. A "vitreous state" is an amorphous solid formed from a liquid without the formation of crystals. As the term is used herein, a vitreous state refers more particularly to a solid formed from a liquid without the formation of ice crystals. Vitrification is accomplished by reducing the temperature of a solution below the glass transition temperature (Tg) for that solution when the Tg is lower than the homogeneous nucleation temperature for that solution, such that a vitreous state is established for the solution and for cells, tissue or organs suspended in or perfused with that solution. That is, "vitrification," as it is used herein when a cell, tissue or organ is vitrified occurs both inside cells, tissues or organs (i.e., inside the cells that comprise tissues and organs) and in the surrounding material (i.e., in the hypothermic storage solution). Vitreous storage is preferably performed at a temperature below the Tg for a hypothermic storage solution.

"Hypothermic storage solution" refers to a solution in which cells, tissues, or organs can be stored at temperatures below physiological temperature. Hypothermic storage solutions for the methods described herein have a Tg lower than the homogeneous nucleation temperature, such that the solution will form a glass, rather than a crystalline solid when temperature is reduced below the Tg. Vitrification, rather than crystal formation, occurs in a hypothermic storage solution due to the presence of one or more agents that inhibit ice crystal formation at temperatures higher than Tg. Hypothermic storage solutions having this property are known in the art. Preferred hypothermic storage solutions are described herein below. The term hypothermic storage solution does not include tissue culture growth medium alone.

As used herein, a "composition" can have one or more component elements.

As used herein, a "vitrification composition" is a composition comprising one or more agents that alone or together have the effect of altering the Tg of a solution comprising such composition. A given vitrification composition has a concentration at which it will alter the Tg of a given solution and depress the freezing point for that solution. At that concentration, which is sufficient for the vitrification of the solution, reducing the temperature to the Tg or below will result in the vitrification of the solution. Examples of agents that have the effect of alter the freezing point and Tg of a solution above the homogeneous nucleation temperature are provided herein below.

As used herein, the term "inhibit" means to reduce an activity by at least 5%, and preferably more, e.g., 20%, 30%, 40%, 50%, 60%, 70%, 80%, 90% or more, up to and including 100% relative to that activity that is not subject to such inhibition. Thus, an agent that inhibits apoptosis inhibits apoptosis by at least 5% relative to a sample subject to thesame apoptotic stimulus but absent the agent.

As used herein, the term "enhance" means to increase an activity by at least 5%, and preferably more, e.g., 20%, 50%, 75% or even 100% or more (e.g., 2×, 5×, 10×, etc.) relative to that activity that is not subject to such enhancement.

As used herein, an "anti-apoptotic composition" or the equivalent alternative term "composition that inhibits apoptosis" refers to a composition that inhibits apoptosis triggered by or accompanying vitrification or vitreous preservation of a cell, tissue or organ. An "anti-apoptotic composition" as used herein will reduce hypothermic-induced apoptosis by at least 5% (i.e., will increase cell survival by at least 5%), relative to a sample preserved without such agent, and can decrease one or more specific indicia of apoptosis, e.g., DNA laddering, TUNEL signal, caspase activity, annexin V binding, etc. An anti-apoptotic composition will comprise one or more anti-apoptotic agents. Anti-apoptotic agents fall into two broad classes, those that interact with a polypeptide that participates in an apoptotic pathway (e.g., participation in the cellular generation, propagation or execution of an apoptotic signal) and those that inhibit by other means, for example, frequently by avoiding or countering the effects of oxidative stress that tend to activate the apoptotic program. In the first broad class of agents, which target polypeptide factors, there are two sub-categories: a) agents that inhibit the activity of polypeptides that participate in the pathway, and b) agents that maintain or potentiate the activity of polypeptides whose normal role it is to prevent apoptosis. In one aspect, the invention contemplates the use of an anti-apoptotic agent or composition that only targets one or more polypeptide targets. In another aspect, the invention contemplates that use of an anti-apoptotic agent or composition that only targets other aspects of the apoptotic process, e.g., changes in redox status or potential. In another aspect, the invention contemplates the use of an agent or composition that acts upon either of these sites.

It is specifically contemplated that a composition that inhibits apoptosis will comprise a combination of agents, wherein each agent alone may or may not have the necessary apoptotic effect, but wherein the combination of such agents has the necessary inhibitory effect on apoptosis. Effects of such a combination can be, for example, additive or synergistic.

As used herein, the term "maintains or potentiates the activity of a polypeptide" refers to compositions or agents that prevent a decrease or cause an increase in a given activity of a given polypeptide. For example, when a polypeptide is active in preventing apoptosis, an agent that maintains or potentiates the activity of that polypeptide prevent a decrease in the anti-apoptotic activity of that polypeptide, thereby preventing or inhibiting apoptosis (i.e., inhibiting apoptosis by at least 10% relative to a sample not treated with that agent and subject to the same apoptotic stimulus).

As used herein, the term "composition that interacts with a polypeptide that participates in an apoptotic pathway" refers to a composition comprising one or more agents that, alone or together, physically interact with a polypeptide target in the apoptotic pathway such that apoptosis is decreased or inhibited. Non-limiting examples of such polypeptides are listed in Table IA and B.

As used herein, the term "polypeptide that participates in an apoptotic pathway" refers to a polypeptide, at least one function of which is to promote or inhibit apoptosis. Thus, one class of such polypeptides includes a polypeptide that acts to promote apoptosis—the inhibition of its function or expression, e.g., a specific protease activity, leads to an inhibition of apoptosis. Another class of such polypeptides includes a polypeptide that acts to inhibit apoptosis—the activation or maintenance of its function or expression, e.g., Bcl-2 activity, also leads to an inhibition of apoptosis.

As used herein, the term "antioxidant" refers to an enzyme or other organic molecule that can counteract or inhibit the damaging effects of oxygen in tissues. Thus, an antioxidant Although the term technically applies to molecules reacting with oxygen, as the term is used herein, antioxidant also refers to molecules that protect from damage by any free radical. A "free radical scavenger" either reduces a free radical by donation of an electron or consumes the free radical by reaction with it in competition with other possible targets of free radical attack.

DESCRIPTION

The invention provides a method of preserving a eukaryotic cell, tissue or organ by contacting the cell, tissue or organ with a hypothermic storage solution containing an agent that inhibits apoptotic cell death, and vitrifying the cell, tissue or organ and the hypothermic storage solution surrounding or perfusing the cell, tissue or organ. The vitrification is accomplished through use of a hypothermic storage solution that has a glass transition temperature (Tg) lower than the homogeneous nucleation temperature of the solution but in which the presence of a vitrification composition inhibits crystalline ice formation. Reduction of the temperature of a sample in such a solution to below the glass transition temperature results in the vitrification of the solution and the cell, tissue or organ in that solution. Under these circumstances, there is no crystalline ice formation in or around the cells as the sample becomes a solid. The inclusion of one or more anti-apoptotic agents aids in preventing the apoptotic cell death that normally occurs subsequent to this type of preservation.

Hypothermic storage solutions:

Hypothermic storage solutions for use in the methods described herein have a Tg lower than their homogeneous nucleation temperature. Such solutions will form a glass or vitreous solid upon reduction in temperature below the Tg, without the accompanying formation of crystalline ice. When cells, tissue or organs are placed in or perfused with a hypothermic storage solution, the cells, tissue or organs will vitrify (i.e., intracellular vitrification) along with the surrounding hypothermic storage solution, when the temperature is reduced below the Tg for the hypothermic storage solution.

Hypothermic storage solutions for the methods described herein have a Tg lower than the homogeneous nucleation temperature because of the presence of a vitrification composition. A vitrification composition comprises one or more agents that alone or together have the effect of raising the Tg of a solution. At that concentration, which is "sufficient for the vitrification of the solution," reducing the temperature to the Tg or below will result in the vitrification of the solution. A key property of an agent that raises the Tg of a solution, i.e., a vitrification agent in a vitrification solution, is the ability to bind up water molecules. By binding up water molecules in solution, such agents tend to prevent the alignment of water molecules necessary for ice crystal formation. For example, trehalose binds~13 moles of water per mole of trehalose, and DMSO binds~7 moles of water per mole of DMSO. Each of these agents are examples of agents of a vitrification composition according to methods described herein.

Another property agents for raising the Tg of a solution (i.e., agents for a vitrification solution) tend to have is that they increase the viscosity of the solution. High viscosity tends to interfere with ice nucleation in part by slowing the motion of molecules necessary for initiating an alignment into a crystalline ice structure. Such agents include, for example, hydroxyethyl starch, glycerol, polyvinyl pyrrolidone, polyethylene glycol, and polyethylene oxide. Of course, many agents that increase the viscosity of a solution also have high affinity for water molecules, so these are by no means meant to be exclusive categories of agents.

In addition to their effect on Tg, agents in a vitrification composition according to the methods described herein should have low toxicity at the concentrations and temperatures used for vitrification and hypothermic storage. It is noted that an agent that may be toxic at physiological temperatures may not necessarily be toxic at hypothermic storage or vitrification temperatures or under conditions of limited time of exposure.

Non-limiting examples of agents for a vitrification composition according to the methods described herein include sucrose, trehalose, lactose, glucose, and other carbohydrates, DMSO, propylene glycol, ethylene glycol, dextrans, glycerol, hydroxyethyl starch, polyvinyl pyrrolidone, formamide, 1-2-propanediol, ethanol, methanol, other alcohols, and polyethylene oxide. The concentrations at which these agents will be used can vary with the identity of the agent. For example, the carbohydrates, glycols and dextrans will frequently be present at concentrations of 30% to 60% (w/v), while agents such as DMSO will most often be present at lower concentrations (e.g., approximately 5–15%), but can exceed 50%.

Commercially available hypothermic storage solutions or other solutions that provide, for example, necessary electrolyte, oncotic and buffering conditions for hypothermic storage may be adapted for use in the methods described herein. These may include, but are not limited to, the hypothermic storage solutions marketed under the trade names HypoThermosol™, CryoStor™, Unisol™, Viaspan™ (University of Wisconsin Solution), Cellvation™, Plegisol™, Cardiosol™, and HTK™.

Vitrification:

Vitrification, according to the methods described herein, involves the use of a hypothermic storage solution that forms a glass, rather than a crystalline solid when exposed to low temperatures, specifically, temperatures below the Tg.

Vitrification, as the term is used herein, involves the non-crystalline liquid to solid (amorphous) phase transition of both the intracellular contents of cells and the surrounding or perfused hypothermic storage solution. This vitrification thus does not involve the formation of ice crystals within or outside of cells, tissues or organs placed into or perfused with such a solution. This is in contrast to cryopreservation, in which the contents of some proportion of the cells vitrifies, yet ice crystals are permitted to form outside of such cells.

The process of vitrification according to the invention involves the steps of contacting the cells, tissue or organ with the hypothermic storage solution meeting the requirements described herein that contains one or more agents that inhibit apoptosis, and then reducing the temperature below the Tg of the solution, such that a vitreous solid is formed. The rate of cooling will depend upon the vitrification solution, but is generally in the range of 1° C. to 50° C. per minute, most often about 1° C. to 20° C. per minute, e.g., about 1° C. per minute, about 5° C. per minute, about 10° C. per minute, about 15° C. per minute or about 20° C. per minute. The skilled artisan can identify an optimal rate of cooling for a given combination of vitrification solution and tissue.

Vitrification can be monitored in several ways. One of the simplest means is to observe the transmission of light by the vitrified solution. A vitrified solution is a glass that will transmit light more efficiently than a solution with crystalline ice. Thus, the transmission or absorbance/scattering of visible light can be used to monitor vitrification. Alternatively, differential scanning calorimetry (DSC) can be used to evaluate Tg and to determine whether a solid is vitrified. As a vitrified substance is warmed above the Tg, there is an increase in the heat capacity of the substance. The temperature at the midpoint of the increase in heat capacity that occurs as a sample makes the transition between the vitreous state and the non-vitreous state is the Tg of the solution. Vitrification is monitored by evaluating the heat flow characteristics of a sample being evaluated for vitrification as it is heated from a temperature below the Tg to a temperature above the Tg. In a plot of heat flow versus temperature, an increase in the rate of heat flow over this temperature gradient is indicative that the solution was vitrified. That is, the heat flow curve of a vitrified sample is generally horizontal (approximately zero slope) until just before the Tg is reached, then will have a positive slope through the glass phase transition, and will return to a horizontal slope after the transition. This type of curve for a plot of heat flow versus temperature as the material is warmed about Tg indicates that the solution was vitrified. Equipment for DSC is available, for example, from Perkin Elmer (e.g., the Perkin Elmer DSC7 Differential Scanning Calorimeter).

The vitrified sample is then stored below the Tg, often at or below −196° C. (liquid nitrogen temperature). Further reduction in temperature below Tg is desirable because amorphous (vitrified) pure water re-crystallizes beginning at approximately −130° C. While neither the hypothermic storage solution nor the intracellular environment of cells, tissues or organs vitrified in such a storage solution are pure water, it can be helpful to maintain the samples below this temperature to avoid possible devitrification and re-crystallization. Such preservation maintains vitrification without permitting crystallization within and outside of cells.

The step of contacting cells, tissues or organs with a hypothermic storage solution will differ depending upon whether the sample is cells, a tissue or an organ. For example, cells or relatively thin (e.g., up to about 2–5 mm) or porous tissues (e.g., skin or artificial skin) can simply be immersed in the hypothermic storage solution prior to chilling to cause vitrification. This immersion is preferably performed at or near 0° C. The length of time necessary for immersion will clearly vary with the thickness of the tissue, with longer times necessary as the tissue becomes thicker. One of skill in the art can readily evaluate and adjust the time necessary for the immersion of a given sample or type of sample by evaluating the survival, recovery and degree of apoptosis occurring in samples immersed for varying lengths of time before vitrification.

For organs, e.g., kidney, liver, heart, lung, etc., it can be necessary to perfuse the organ with the hypothermic storage solution. Methods for organ perfusion vary for different organs but are well known in the art. For perfusion of organs, an important parameter is the viscosity of the solution. More porous organ tissues (e.g., liver) can be perfused with relatively higher viscosity solutions than can less porous tissues (e.g., heart). Because of differences in the ability to perfuse different tissues, it may be necessary in some cases to perfuse with an increasing gradient, or with stepwise increases, of the concentration of hypothermic storage solution until a concentration is achieved such that the tissue will vitrify, rather than freeze upon subsequent reduction of temperature.

Apoptosis and Anti-Apoptotic Agents:

The precise cellular mechanisms regulating apoptosis are not completely known. However, various aspects of the apoptotic pathway have been elucidated. For example, alteration of the ionic environment may be necessary to activate or inhibit the endonucleases relevant to the process of apoptotic nuclear degradation (e.g., physiologic concentrations of $Zn++$ are known to inhibit DNA fragmentation and apoptosis). Treatment of certain cells with inhibitors of macromolecular synthesis, such as Actinomycin D to block RNA synthesis or cyclohexamide to block protein synthesis, induces apoptosis. Completion of the apoptotic process appears to depend upon the regulated expression of various gene products associated with the promotion or suppression of gene activated cell death, particularly gene products involved with cell cycle regulation. For example, overexpression of the cell-death inhibiting agents Bcl-2 and Bcl-xL prevents the release of cytochrome C. Cytochrome C is thought to activate the caspases, a group of proteases known for cleaving substrates responsible for the changes associated with apoptosis. Enhanced levels of Bax, a pro-apoptotic member of the Bcl-2 family, promote cytochrome C release and subsequent apoptosis of cells. Specific regulation of the early response genes c-myc, c-jun and c-fos may promote either cell growth or cell death, depending upon the circumstances surrounding their expression. Another trigger for apoptosis involves oxidative stress. In this regard, antioxidants and free-radical scavengers have been demonstrated to inhibit the initiation of apoptosis. Thus, programmed cell death involves an intricate cascade of cellular events.

The inventors have discovered that hypothermic storage is among the numerous triggers for apoptosis. In particular, the vitrification of cells tends to cause a proportion of the cells to undergo apoptosis when they are removed from the vitreous state. While it is not known exactly what is the molecular mechanism of the triggering event for vitrification-induced apoptosis, the inventors have determined that the inclusion, in the hypothermic storage solution used for vitrification, of one or more agents that alone or collectively inhibit apoptosis can increase the survival and recovery of vitrified cells.

There are a number of agents known to inhibit apoptosis. Anti-apoptotic agents finding use in the methods described herein can function at any stage of the apoptotic pathway, e.g., by modulating the function or expression of one or more nuclear or cytoplasmic polypeptide mediators of the pathway (e.g., gene products in the regulatory cascade such as Bcl-xL, Bcl-2 or Bax, cytochrome C, caspase enzymes, etc.) or by avoiding or countering the effects of oxidative stress known to trigger apoptosis (e.g., through use of antioxidants, free radical scavengers or agents that modulate the function or expression of nitrous oxide synthase).

One useful way to categorize inhibitors of apoptosis is to consider those that interact with a cellular polypeptide factor that participates in the generation, propagation or execution of an apoptotic signal to be one category, and those that inhibit by other means as a second category. In the first category, the interaction of the agent with the polypeptide factor is a physical, i.e., binding, interaction. For example, an agent that physically interacts with and inhibits the function of a caspase enzyme would fall into this category. In the second category the agent need not necessarily interact with or bind a polypeptide, but rather acts by, for example scavenging free radicals or maintaining the redox status quo. Examples of agents in the second category include, for example, Vitamin E and other agents listed in Table II.

According to the methods described herein, a composition that inhibits apoptosis comprises at least one agent that reduces the extent of apoptotic cell death, but is specifically contemplated to comprise, for example, two or more such agents, wherein each such agent preferably, but not necessarily, interacts with a different part of an apoptotic pathway. In another aspect, it is contemplated that the composition comprises two agents that together have an inhibitory effect on apoptosis that neither has on its own, or that together have an effect that is synergistic.

Exemplary cellular polypeptide targets involved in the promotion of apoptosis are listed in Table IA. In one aspect, an anti-apoptotic agent for use in the methods described herein can act on one or more of these cellular polypeptide targets. Table IB also lists exemplary targets involved in the prevention of apoptosis. In another aspect, an anti-apoptotic agent can act to increase or stabilize the activity of one or more of these cellular polypeptide targets.

As noted, an important class of anti-apoptotic agents is the caspase inhibitors, a number of which are known and commercially available. One class of caspase inhibitors comprises fluoromethylketone (FMK) derivatives of peptides that mimic the recognition and cleavage sites for the target caspase enzymes. Among these are, for example: caspase-1 inhibitor YVAD-FMK (benzyloxycarbonyl tyrosylvalylalanyl aspartic acid fluoromethyl ketone), which irreversibly binds activated caspase 1; caspase-3 inhibitor DEVD-FMK (benzyloxyycarbonyl aspartyl glutamylvalylaspartic acid fluoromethyl ketone), which irreversibly binds activated caspase 3 but also inhibits caspase 7, caspase 10, and caspase 6 in decreasing order of binding affinity; caspase-6 inhibitor VEID-FMK (benzyloxycarbonyl valylglutamyl isoleucylaspartic acid fluoromethyl ketone), which irreversibly binds activated caspase 6 and also inhibits caspases 3, 7, and 8 in decreasing order of binding affinity; caspase-8 inhibitor LETD-FMK (benzyloxycarbonyl leucylglutamylthreonylaspartic acid fluoromethyl ketone), which irreversibly binds activated caspase 8, and also binds caspase 1 and caspase 10 with lower affinity; caspase-9 inhibitor LEHD-FMK (benzyloxycarbonyl leucylglutamyl-histidylaspartic acid fluoromethyl ketone), which irreversibly binds caspase 9 and also binds caspases 4, 5 and 6. Additional FMK-peptide derivatives that inhibit caspases include, but are not limited to caspase-2 inhibitor VDVAD-FMK, caspase-4 inhibitor Z-LEVD-FMK, caspase-5 inhibitor WEHD-FMK, caspase-10 inhibitor AEVD-FMK and caspase-13 inhibitor LEED-FMK. These caspase inhibitors, and cocktail mixtures of them are commercially available from, for example, Gentaur Molecular Products (Brussels, Belgium).

Additional anti-apoptotic agents include the calpain inhibitors (e.g., Calpain Inhibitor ZLLT-FMK) and the cathepsin B&L inhibitor Z-Phe-Phe-FMK. These inhibitors are also available from Gentaur Molecular Products. Others include Calpain Inhibitor I (N-Acetyl-LeuLeu-norleucinal, available from Roche Diagnostics), Calpain Inhibitor II (N-Acetyl-Leu-Leumethioninal, available from Roche Diagnostics), and CTX295 (a dipeptide alpha-ketoamide compound which inhibits calpain (DiBiasi et al., 2001, J. Virol. 351–361)).

Nitrous oxide synthase inhibitors can also be used as anti-apoptotic agents. Non-limiting examples include dimethylarginine, 7-nitroindazole, L-NAME ($N^G$-nitro-L-arginine methyl ester), LNMMA (monomethyl L-arginine), L-NNA ($N^G$-nitro-L arginine) and MITU (S-methyl isothiourea). These are available from various commercial sources.

A non-limiting list of additional anti-apoptotic agents is also provided in Table II.

The amount of an anti-apoptotic agent or agents included in a hypothermic storage solution according to the methods described herein will vary depending on the nature of the inhibitor and its target, if the target is known (there is no requirement that the specific target of an apoptotic inhibitor be known in order for the inhibitor to be used in a method as described herein). Generally, the amount of anti-apoptotic agent will be that amount or concentration determined by the user to provide at least 5% (and preferably greater) inhibition in apoptosis following removal from the vitrified state relative to a sample that was vitrified in the absence of the inhibitor or inhibitors. The concentration of anti-apoptotic agent for use in the methods described herein will further not be associated with significant (i.e., greater than 2% cell death over the course of treatment or contact) toxic effects. The level at which an agent becomes toxic will vary with the agent and will generally be known or readily determined by one of skill in the art.

TABLE I

| Target | Definition | Pathway Location (Initiation, Execution, Termination) |
|---|---|---|
| A. Cellular Targets Involved in the Promotion of Apoptosis | | |
| Caspases | (Cystine Proteases) | Initiation, Execution, Termination |
| ROCK | | Termination |
| CAD | (Caspase Activated DNAse) | Termination |
| ASK1 | | Initiation, Execution |
| JNK | (Jun Kinase Family) | Initiation |
| Fas | | Initiation |
| FADD | (Fas Activated Death Domain) | Initiation |
| TNF | (Tumor Necrosis Factor) | Initiation |
| TRADD | (TNF Receptor Activated Death Domain) | Initiation |
| RIP | (receptor Interacting Protein) | Initiation |
| DAXX | | Initiation |
| Granzyme B | | Initiation |
| Bad | (Mitochondrial Pro-apoptotic protein) | Initiation, Execution |
| Bax | (Mitochondrial Pro-apoptotic protein) | Initiation, Execution |

TABLE I-continued

| Target | Definition | Pathway Location (Initiation, Execution, Termination) |
|---|---|---|
| Bid | | Initiation, Execution |
| Cytochrome C | | Initiation, Execution |
| AIF | (Apoptosis Initiation Factor) | Initiation, Execution |
| MAPK | (Mitogen Activated Protein Kinase Family) | Initiation |
| Calpain | (Serine Proteases) | Initiation, Execution, Termination |
| Caspathin | | Initiation, Execution, Termination |
| Nitric Oxide | | Initiation |
| PARP | (Poly-ADP Ribose Polymerase) | Termination |
| DFF | (DNA Fragmentation Factor) | Termination |
| Smac/Diablo | Mitochondrial Pro-apoptotic protein | Initiation, Execution |
| B. Cellular Targets Involved in the Prevention of Apoptosis | | |
| Bcl-2 | (Mitochondrial Anti-apoptotic protein) | Initiation, Execution |
| Bcl-x | (Mitochondrial Anti-apoptotic protein) | Initiation, Execution |
| IAP | (Inhibitor of Apoptosis Protein) | Initiation, Execution |
| RAS | Receptor mediated pro-survival signal | Initiation |
| AKT | Anti-apoptosis signal | Initiation, Execution |
| TRAF2 | (TNF Receptor Associated Factor 2) | Initiation |
| NIK | TNFR2 pro-survival signal | Initiation |
| IKK | Anti-apoptosis signal | Initiation |
| NFKB | Pro-Survival and Transcription Factor | Initiation, Execution |

TABLE II

Free Radical Scavengers and Other Anti-apoptotic Agents

Flavonoids
Vitamin E
Vitamin C
Vitamin D
Beta Carotene (Vitamin A)
Pycnogenol
Super Oxidedismutase
N-Acetyl Cysteine
Selenium
Catechins
Alpha Lipoic Acid
Melatonin
Glutathione
Zinc Chelators
Calcium Chelators
L-Arginine

TABLE III

Proteinases Classification Based on Catalytic Properties

| Proteinases Class | Selected Example |
|---|---|
| Aspartic | Cathepsins D and E; pepsin; rennin |
| Cystiene | Calpains; caspases; cathepsins B, H, K, L, and S; deubiquitinases; papain |
| Metallo | Astactin; carboxypeptidases; collagenase; gelatinase; hedgehog protein; meprin; stromelysin; thermolysin; tolloid protein |
| Serine | Cathepsin G; chymotrypsin; granzyme; elastase; kallikrein; subtilisin; proteinase K; thrombin; ticorn protease; tripeptidyl-peptidase II; trypsin |
| Threonine | Proteasome |

TABLE IV

Inhibitory Agents of Proteinases

| Protease Class | Inhibitor |
|---|---|
| Serine Proteinases | AEBSF; Antipain; APMSF; Aprotinin; Benzamidine; Chymostatin; DCI; DFP; Ecotin; Elastinal; Leupeptin; PMSF; Soybean Trypsin Inhibitor; TLCK; TPCK |
| Aspartic Proteinases | EPNP; Pepstatin A |
| Metallo Proteinases | Bestatin; EDTA; Epibestatin; 1, 10-Phenanthroline; Phosphoramidon |
| Cysteine Proteinases | Antipain; Chymostatin; Cystatin; E-64; Leupeptin; NCO-700; Z-Leu-Leu-Try-CHN$_2$; Z-Leu-Val-Gly-CHN$_2$; Z-Phe-Ala-CHN$_2$ |
| Caspase Family Inhibitors | CHO; FMK (Fluoromethyl ketones); CMK (Chloromethyl ketones); DCB (2,6-dichlorobenzoyloxmethyl ketone); AOM (2,6-dimethylbenzoyloxmethyl ketone); FAOM (2,6-bis(trifluoromethyl)benzoyloxmethyl ketone) |
| Calpain Family Inhibitors | Leupeptin; Calpain inhibitor I, II, III, IV, V; Calpeptin; Loxastatin; Dipeptidyl alpha-ketoamides; Dipeptidyl phosphorus derivatives; Peptide chloromethyl ketones; peptide diazomethylketones; Peptide disulfides; Peptide fluoromethyl ketones; Peptide methyl esters; Peptide acycloxymethyl ketones; Quinoline carboxamides |
| Proteasome Proteinases | Aclacinomycin A; Gliotoxin; Lactacystin; Peptide aldehydes, Peptide chloromethyl ketones; Peptide diazomethyl ketones; Peptide alpha-beta-epoxy ketones; Peptidyl boronic acids; Peptide ethyl-ketoamides; Peptidyl-alpha-keto aldehydes, Peptidyl-vinal sulfones |

Measurement of Apoptosis:

There are a number of ways available for one to measure the extent of apoptosis occurring following the vitrification of a sample containing cells. As noted, one of the hallmarks of apoptosis is a regular DNA fragmentation pattern leading to a "ladder" when genomic DNA is subjected to gel electrophoresis. This assay is well known in the art, and can be performed as described in U.S. Pat. No. 6,045,990.

Another assay useful for more quantitative measurement of apoptosis is the TUNEL assay (Terminal deoxynucleotidyl transferase mediated dUTP nick end labeling). This assay measures the enzymatic incorporation of labeled dUTP at the nick or breaks in DNA that accompany apoptosis. The assay is well known to those of skill in the art, and kits for performing the assay are available, for example, from Intergen (ApopTag™ kit, Intergen Company, Purchase, N.Y.).

Alternatively, one may directly assay caspase activity. Kits for this are also commercially available, e.g., from Promega (Madison, Wis.).

Other assays for apoptosis are also known to those of skill in the art. For example, Annexin V binding to cells can be measured. One of the early events of apoptosis is the loss of membrane asymmetry of phospholipids. Phosphotidylserine, normally located in the inner leaflet of the membrane, redistributes and appears in the outer leaflet at the early stage of apoptosis. Annexin V binds specifically to phosphotidylserine on apoptic cell surfaces in the presence of calcium, and can be used as a marker for apoptosis. Binding can be measured by monitoring a fluorescent tag on the Annexin V, e.g., fluorescein.

Removal from the Vitreous State

The process for the removal of cells, tissues or organs from the vitreous state will vary depending upon the cell, tissue or organ preserved. The general process involves warming the sample above the Tg and freezing point, followed by dilution or rinsing to remove the hypothermic storage solution and vitrification agents, followed by re-establishment in culture or by implantation into a recipient. Rinsing can be performed by simple immersion (e.g., for cells or relatively thin tissues) or by perfusion (e.g., for organs). While minimizing time out of standard culture conditions or a recipient individual is always desirable, it may be advantageous to remove hypothermic storage solution by stepwise immersion or perfusion with gradually reduced concentrations of vitrification agents. In such circumstances, it can be advantageous to include an anti-apoptotic composition in the rinse solution or solutions. In fact, an anti-apoptotic composition can advantageously be added to any such rinse solution.

Measurement of Hypothermic Storage Efficiency:

The term "hypothermic storage" encompasses storage for a matter of hours or for a matter of weeks, months or years. The level of cell survival acceptable for such storage will depend upon the cell, tissue or organ type stored and the reason for its storage (e.g., transplantation versus forensic uses), but will advantageously be higher than is practicable using prior art technologies. When a cell, tissue or organ is used for human transplantation, clearly the higher the survival and ensuing function, the better. Generally, however, hypothermic storage is considered successful if it is accompanied by death of about 25% or fewer of the cells, preferably 15% or less, and most preferably less than 5%, up to and including full viability and function. In some cases, such as organ preservation, due to the invasive nature of the tests, it is not always practical to determine the level of cell survival. Thus, while in the laboratory setting 75% cell survival is considered to identify successful candidate preservation solutions and methods, in cases such as organ (e.g., liver or kidney) transplantation, organ function of 50% or higher is considered to be a successful transplant. The 50% or higher function is judged by improvement in patient health and overall organ function, which is a relative interpretation of response and function.

The cold-storage efficacy of numerous cell preservation solutions can be assessed using a number of assays. Such assays include enzyme synthesis (Pahernik et al., 1996, Cryobiology 33: 552), potassium content (Fisher et al., 1996, Cryobiology 33: 163), trypan blue exclusion (Rodriguez et al., 1995, Cell Transplant. 4: 245), neuronal outgrowth and myelination (Levi et al., 1994, Glia 10: 121), contraction (Lopukhin et al., 1996, Cryobiology 33: 178), ATP content (Zhang et al., 1996, J. Surg. Res. 63: 314), and ultrastructure (Carbognani, et al., 1995, J. Cardiovasc. Surg. 36: 93). These assays can be considered either viability or functional assays. Thus, the maltose tolerance test used by Katz et al. (Katz et al., 1995, Transplantation 59: 694) on the small intestine could be considered a functional assay; whereas the trypan blue test used by Rodriguez et al. (Rodriguez et al., 1995, supra) is strictly a viability assay.

A preferred assay for viability uses the non-toxic dye ALAMAR BLUE™. The assay using ALAMAR BLUE™ measures viability by the metabolic conversion of the agent to a fluorescent form detectable with standard fluorescence detection equipment. The assay does not indicate whether or not test cells are functioning in a tissue specific manner. However, one of the key attributes of the ALAMAR BLUE™ assay that is not shared by most of the other viability or function assays described previously is the ability of ALAMAR BLUE™ to be used repetitively, day after day, as a non-toxic indicator. This has been shown to be critically important to some cold-stored tissues such as human skin cells.

An example of the conditions for ALAMAR BLUE™ viability testing following vitreous storage is as follows.

Cells (e.g., cultured cells or cells isolated from a patient) are washed with isotonic buffer solution (e.g., phosphate buffered saline, Hanks' Balanced Salt Solution (HBSS), etc.) and the medium is replaced with a hypothermic storage solution containing a composition that inhibits apoptosis (i.e., containing at least one apoptosis inhibiting agent). The cell sample is vitrified and maintained for a given time period at low temperature, e.g., −196° C., after which the sample is warmed such that the solution returns to the liquid state. The hypothermic storage solution is removed, cells are washed in isotonic buffer solution or cell culture medium and plated for growth in appropriate cell culture medium. After a given period of time (generally about 24 hours, but advantageously later, e.g., 48 hours or more) medium is removed from the recovered cultures, and a 1:20 dilution of ALAMAR BLUE™ (Accumed International, Westlake, Ohio) in HBSS without phenol red is placed on the cells. Fluorescence of the converted dye is measured using, for example, a CytoFluor 2350 (Millipore Corporation, Bedford, Mass.) or a CytoFluor II (PerSeptive Biosystems, Inc., Cambridge, Mass.) apparatus with a 530 nm excitation/590 nm emission filter set. Following the assay, cells can be provided with fresh medium and re-cultured, with repeat assays at later times as desired.

Another means of monitoring the viability of recovered cells, tissues or organs uses the dye Calcein-AM (Molecular Probes, Eugene, Ore.), which monitors membrane integrity. Calcein-AM is suspended at 1 mg/ml in DMSO and then mixed with HBSS at 1:100. This solution is then contacted with recovered cells for one hour, followed by washing with HBSS. Fluorescence of the retained dye, indicative of intact living cells, is then measured using a 485 nm excitation/530 nm emission filter set.

The methods described herein encompass the preservation of various organs, tissues and cells by vitrification. Organs, including but not limited to lung, liver, heart, kidney, gut, eye and skin can be preserved according to the invention prior to transplantation in a recipient patient. Tissues such as bone marrow and cells such as erythrocytes and leukocytes can be preserved for long term storage according to the invention. For example, tissues for forensic and pathology records may be preserved without significant loss of viability. Cell lines for therapeutic and research interests can be preserved for long periods by applying the invention. Of particular interest is long term preservation of gametes and embryos for reproductive procedures such as in vitro fertilization. It is contemplated that variations of the invention can be applied for long-term preservation of entire multicellular organisms.

Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims. All literature and patent references cited herein are hereby incorporated herein in their entirety by reference.

What is claimed is:

1. A method of preserving a eukaryotic cell, tissue or organ comprising:
   a) contacting said cell, tissue or organ with a hypothermic storage solution, wherein said solution comprises:
      i) a composition that inhibits apoptosis; and
      ii) a concentration of a vitrification composition that is sufficient for vitrification of said solution; and
   b) vitrifying said cell, tissue or organ, wherein said vitrification occurs both within said cell, tissue or organ and in said hypothermic storage solution comprising and comprised by said cell, tissue or organ;
   wherein said composition that inhibits apoptosis comprises an agent that interacts with a polypeptide that participates in an apoptotic pathway; and
   wherein said agent is a calpain inhibitor and is selected from the group consisting of leupeptin, calpain inhibitors I, II, III, IV and V, calpeptin, loxastatin, a peptide chloromethyl ketone and a peptide fluoromethyl ketone.

2. The method of claim 1 wherein said hypothermic storage solution has a glass transition temperature lower than its homogeneous nucleation temperature.

3. The method of claim 1 wherein said vitrification composition comprises one or more agents selected from the group consisting of sucrose, trehalose, lactose, glucose, DMSO, propylene glycol, ethylene glycol, a dextran, glycerol, hydroxyethyl starch, polyvinyl pyrrolidone, formamide, 1-2-propanediol, ethanol, methanol, and polyethylene oxide.

4. A method of preserving a eukaryotic cell, tissue or organ comprising:
   a) contacting said cell, tissue or organ with a hypothermic storage solution, wherein said solution comprises:
      i) a composition that inhibits apoptosis comprising an agent that interacts with a polypeptide that participates in an apoptotic pathway, wherein said agent comprises a calpain inhibitor; and
      ii) a concentration of a vitrification composition that is sufficient for vitrification of said solution; and
   b) vitrifying said cell, tissue or organ, wherein said vitrification occurs both within said cell, tissue or organ and in said hypothermic storage solution comprising and comprised by said cell, tissue or organ.

* * * * *